(12) United States Patent
Rich

(10) Patent No.: US 8,187,888 B2
(45) Date of Patent: *May 29, 2012

(54) FLUIDIC SYSTEM FOR A FLOW CYTOMETER

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/178,776

(22) Filed: Jul. 8, 2011

(65) Prior Publication Data

US 2011/0306031 A1    Dec. 15, 2011

Related U.S. Application Data

(63) Continuation of application No. 11/370,714, filed on Mar. 8, 2006, now Pat. No. 8,017,402.

(51) Int. Cl.
*G01N 35/08* (2006.01)
*G01N 33/48* (2006.01)

(52) U.S. Cl. ............ 436/63; 436/164; 436/177; 422/73; 422/82.05; 422/400; 356/39; 356/72; 356/246; 356/335

(58) Field of Classification Search .................. None
See application file for complete search history.

(56) References Cited

U.S. PATENT DOCUMENTS

| | | |
|---|---|---|
| 3,347,273 A | 10/1967 | Russell |
| 3,601,128 A | 8/1971 | Hakim |
| 3,672,402 A | 6/1972 | Bloemer |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |

(Continued)

FOREIGN PATENT DOCUMENTS

EP            466490 A       1/1992

(Continued)

*Primary Examiner* — P. Kathryn Wright
(74) *Attorney, Agent, or Firm* — Jeffrey Schox

(57) ABSTRACT

The fluidic system of the preferred embodiment includes a sheath pump to pump sheath fluid from a sheath container into an interrogation zone and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The fluidic system is preferably incorporated into a flow cytometer with a flow cell that includes the interrogation zone.

18 Claims, 2 Drawing Sheets

U.S. PATENT DOCUMENTS

| | | |
|---|---|---|
| 5,139,609 A | 8/1992 | Fields et al. |
| 5,150,037 A | 9/1992 | Kouzuki |
| 5,150,313 A | 9/1992 | Van Den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheime |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 * | 1/2004 | Gerner et al. .......... 138/30 |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | Van den Engh et al. |
| 2003/0211009 A1 | 11/2003 | Buchanan |
| 2003/0223061 A1 | 12/2003 | Sebok |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm, Jr. et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |

| | | | | | | |
|---|---|---|---|---|---|---|
| 2006/0219873 | A1 | 10/2006 | Martin et al. | 2011/0008816 A1 | 1/2011 | Ball et al. |
| 2006/0281143 | A1 | 12/2006 | Liu et al. | 2011/0058163 A1 | 3/2011 | Rich |
| 2006/0286549 | A1 | 12/2006 | Sohn et al. | 2011/0061471 A1 | 3/2011 | Rich et al. |
| 2007/0003434 | A1 | 1/2007 | Padmanabhan et al. | | | |
| 2007/0041013 | A1 | 2/2007 | Fritz et al. | | | |

FOREIGN PATENT DOCUMENTS

| | | | |
|---|---|---|---|
| 2007/0096039 A1 | 5/2007 | Kapoor et al. | |
| 2007/0124089 A1 | 5/2007 | Jochum et al. | EP 1391611 A 2/2004 |
| 2007/0127863 A1 | 6/2007 | Bair et al. | EP 1396736 A 3/2004 |
| 2007/0144277 A1* | 6/2007 | Padmanabhan et al. ... 73/864.81 | EP 1521076 4/2005 |
| 2007/0212262 A1 | 9/2007 | Rich | JP 356169978 12/1981 |
| 2007/0224684 A1 | 9/2007 | Olson et al. | JP 04086546 H 3/1992 |
| 2007/0243106 A1 | 10/2007 | Rich | JP 6-194299 * 7/1994 |
| 2008/0055595 A1 | 3/2008 | Olson et al. | JP 06221988 H 12/1994 |
| 2008/0064113 A1 | 3/2008 | Goix et al. | JP 08201267 H 8/1996 |
| 2008/0092961 A1 | 4/2008 | Bair et al. | JP 09288053 H 11/1997 |
| 2008/0152542 A1 | 6/2008 | Ball et al. | JP 10227737 A 8/1998 |
| 2008/0215297 A1 | 9/2008 | Goebel et al. | JP 2001050887 A 2/2001 |
| 2008/0228444 A1 | 9/2008 | Olson et al. | WO 9956052 11/1999 |
| 2009/0104075 A1 | 4/2009 | Rich | WO 0194914 12/2001 |
| 2009/0174881 A1 | 7/2009 | Rich | WO 2005/017499 2/2005 |
| 2009/0201501 A1 | 8/2009 | Bair et al. | WO 2005068971 A 7/2005 |
| 2009/0202130 A1 | 8/2009 | George et al. | WO 2005073694 A 8/2005 |
| 2009/0216478 A1 | 8/2009 | Estevez-Labori | WO 2005091893 A 10/2005 |
| 2009/0260701 A1 | 10/2009 | Rich et al. | WO 2006055722 A 5/2006 |
| 2009/0293910 A1 | 12/2009 | Ball et al. | WO 2007067577 A 6/2007 |
| 2010/0012853 A1 | 1/2010 | Parks et al. | WO 2007100723 A 9/2007 |
| 2010/0032584 A1 | 2/2010 | Dayong et al. | WO 2007103969 A 9/2007 |
| 2010/0118298 A1 | 5/2010 | Bair et al. | WO 2007136749 A 11/2007 |
| 2010/0119298 A1 | 5/2010 | Huang | WO 2008058217 A 5/2008 |
| 2010/0302536 A1 | 12/2010 | Ball et al. | WO 2010101623 A 9/2010 |
| 2010/0319469 A1 | 12/2010 | Rich | |
| 2010/0319786 A1 | 12/2010 | Bair et al. | * cited by examiner |

*30, 40, 41*

*30, 40, 43*

FLUIDIC SYSTEM FOR A FLOW CYTOMETER

CROSS-REFERENCE TO RELATED APPLICATIONS

This application is a continuation of prior application Ser. No. 11/370,714, filed 08 Mar. 2006, which is incorporated in its entirety by this reference.

TECHNICAL FIELD

This invention relates generally to the flow cytometer field, and more specifically to an improved fluidic system in the flow cytometer field.

BACKGROUND

The fluidic system of a conventional flow cytometer incorporates an air and/or vacuum pump to pressurize and pump sheath fluid from a high-pressure container to the interrogation zone of a flow cell. These fluidic systems are typically arduous to assemble (which increases the costs of the flow cytometer), heavy to haul (which limits the repair options), and challenging to calibrate (which induces errors in the data). Thus, there is a need in the flow cytometer field to create an improved fluidic system. This invention provides such improved fluidic system for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

Figure 1:
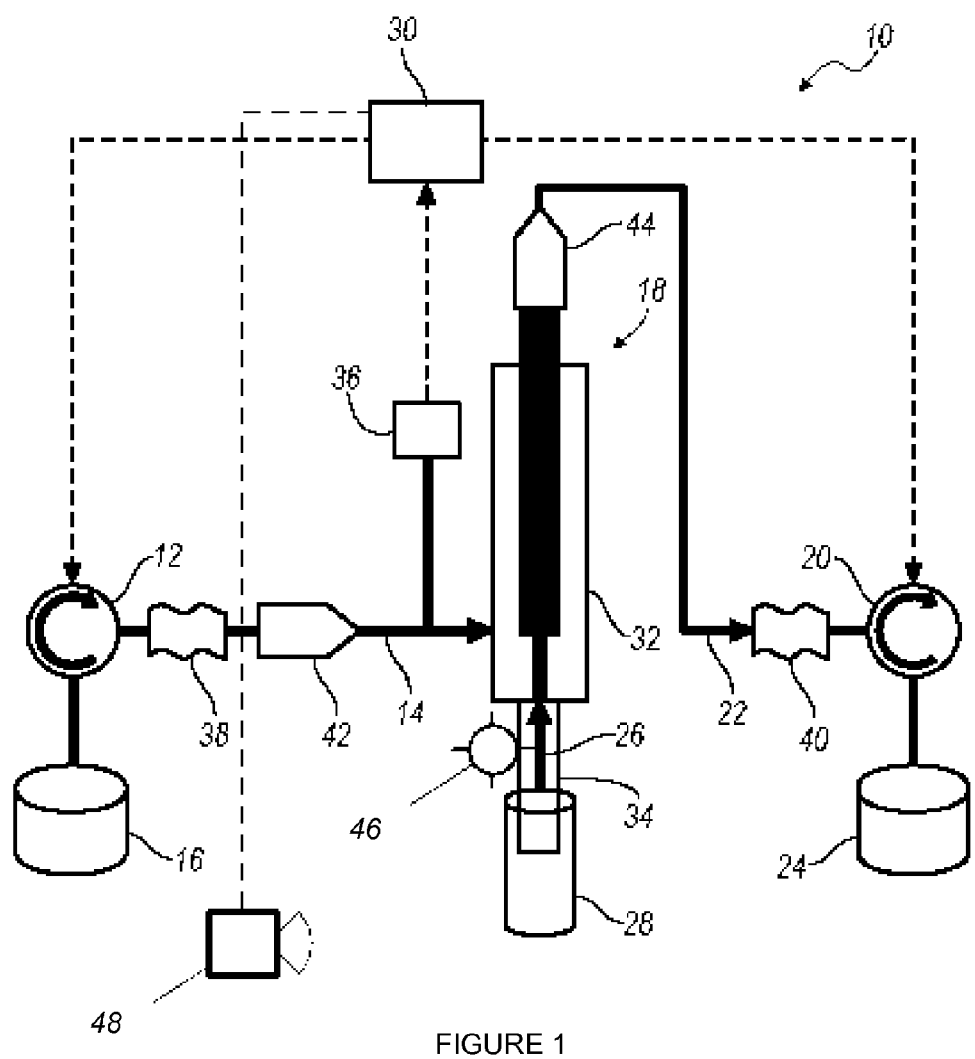
FIG. 1 is a schematic representation of the fluidic system of the preferred embodiment of the invention.
Figure 2:
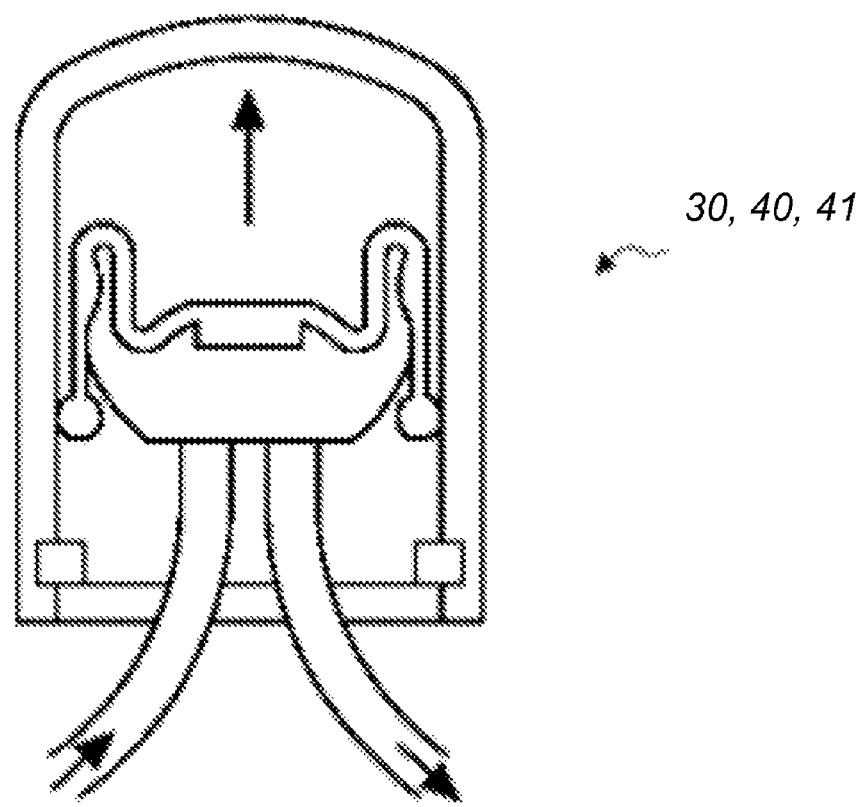
FIGS. 2 and 3 are variations of the fluidic capacitors.
Figure 3:
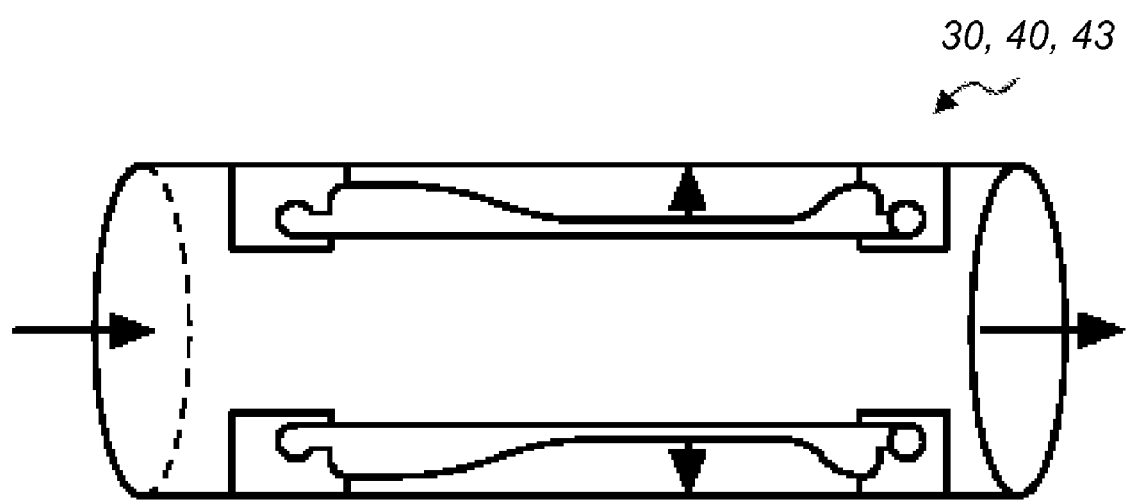

As shown in FIG. 1, the fluidic system 10 of the preferred embodiment includes a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 32, but may alternatively be defined by any suitable system or device. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 34. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 34, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The controller 30 is preferably a proportional-integral-derivative (PID) controller, but may alternatively be a proportional-integral (PI) controller, a proportional-derivative (PD) controller, a proportional (P) controller, or any other suitable controller.

The fluidic system 10 of the preferred embodiment also includes a pressure sensor 36 that functions to measure a pressure of the sheath fluid 14 as close as possible to the inlet for the sample fluid 26. This measured pressure is an adequate estimate for the pressure of the sample fluid 26. The pressure sensor 36 preferably measures a pressure differential between the top of the drawtube 34 near the flow cell 32 and the bottom of the drawtube 34 near the sample container 28, but may alternatively measure a pressure differential between the drawtube 34 and atmosphere. The controller 30 is preferably connected to the pressure sensor 36 and adjusts the flow rate of the sample fluid 26 based on the measured pressure. The controller 30 may alternatively or additionally be connected to other suitable devices to assist in the control of the flow rate of the sample fluid 26. In a first variation, the fluidic system 10 may include a flow meter 46 that functions to measure the flow rate of the sample fluid 26 from the sample container 28 into the interrogation zone 18. In a second variation, the fluidic system 10 may include an input device 48 that functions to receive information related to a fluidic resistance of a drawtube 34 that transports the sample fluid 26 from the sample container 28 into the interrogation zone 18. The input device 48 is preferably an optical device (e.g., a bar code scanner) or an electromagnetic device (e.g., a RFID receiver) that functions to automatically scan and read a code on the drawtube 34. The code is preferably cross-referenced with empirically derived information regarding the fluidic resistance of the drawtube 34. The input device 48 may alternatively be a user-interface device that accepts a code or value related to the fluidic resistance of the drawtube 34. In a third variation, the fluidic system 10 may be substantially self-calibrating according to the following steps: the user places a drawtube 34 of the flow cell 32 into a known fluid (such as buffered saline), the user pumps waste fluid 22 from the interrogation zone 18 into a waste container 24 while maintaining a negligible flow rate of the sheath fluid 14 thereby drawing the known fluid through the drawtube 34 and into the interrogation zone 18, and the fluidic system 10 (through measurement of the flow rate of the waste fluid 22 or any other suitable parameter) estimates the resistance of the drawtube 34. With this estimated resistance of the drawtube 34 for the flow cell 32 combined with the measured pressure of the sheath fluid 14, the controller 30 adjusts the flow rate of the sample fluid 26 with greater accuracy and control.

The fluidic system 10 of the preferred embodiment also includes a first fluidic capacitor 38 located between the sheath container 16 and the interrogation zone 18 and a second fluidic capacitor 40 located between the interrogation zone 18 and the waste container 24. The fluidic capacitors 38 and 40 function to attenuate pulsations within the fluidic system 10. More specifically, the first fluidic capacitor 38 functions to temporarily expand/contract to thereby accumulate/release the sheath fluid 14 and attenuate pulsations within the sheath fluid 14. Similarly, the second fluidic capacitor 40 functions to temporarily expand/contract to thereby accumulate/release the waste fluid 22 and attenuate pulsations within the waste fluid 22. The fluidic capacitors 38 and 40 are selected from the group consisting of bellows-type 41 with a diaphragm, bellows-type 41 without a diaphragm, captive ball-type, and flexible tube-type 43. The fluidic capacitors 38 and 40 are preferably similar to the fluidic attenuators described in U.S. patent application Ser. No. 11/297,667 entitled "Pulsation Attenuator For A Fluidic System" and filed 07 Dec. 2005, which is hereby incorporated in its entirety by this reference. The fluidic capacitors 38 and 40 may, however, be any suitable device to attenuate pulsations within the fluidic system 10.

The fluidic system 10 of the preferred embodiment also includes a valve 42 located between the first fluidic capacitor and the interrogation zone 18, and a valve 44 located between the interrogation zone 18 and the second fluidic capacitor. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22.

The fluidic system 10 of the preferred embodiment is preferably operated with the following steps: (1) pumping sheath fluid 14 from a sheath container 16 into an interrogation zone 18 and pumping the sheath fluid 14 and the sample fluid 26 as waste fluid 22 from the interrogation zone 18 into a waste container 24, thereby drawing sample fluid 26 from a sample container 28 into the interrogation zone 18; and (2) adjusting the flow rate of the sample fluid 26 from the sample container 28 into the interrogation zone 18. As explained above, step (2) preferably includes allowing a substantially adjustable flow rate of the sheath fluid 14 from the sheath container 16 to the interrogation zone 18, while maintaining a substantially consistent flow rate of the waste fluid 22 from the interrogation zone 18 into the waste container 24. The operation of the fluidic system 10 also preferably includes attenuating pulsations within the sheath fluid 14 and the waste fluid 22.

As a person skilled in the art of flow cytometers will recognize from the previous detailed description and from the figures and claims, modifications and changes can be made to the preferred embodiment of the invention without departing from the scope of this invention defined in the following claims.

I claim:

1. A fluidic system for pumping sheath fluid from a sheath container and sample fluid from a sample container into an interrogation zone of a flow cytometer, comprising:
    a sheath pump that pumps sheath fluid from the sheath container into the interrogation zone of the flow cytometer;
    a waste pump that pumps waste fluid from the interrogation zone into a waste container, wherein the sheath pump and the waste pump cooperate to draw sample fluid from the sample container into the interrogation zone;
    a first fluidic capacitor, located between the sheath pump and the interrogation zone, that temporarily expands and accumulates sheath fluid to attenuate pulsations within the sheath fluid;
    a second fluidic capacitor located between the interrogation zone and the waste container and that temporarily expands and accumulates the waste fluid to attenuate pulsations within the waste fluid;
    a drawtube, coupled to the sample container, that conveys the sample fluid from the sample container to the interrogation zone;
    a pressure sensor that measures a pressure differential of the sample fluid between the top of the drawtube and the bottom of the drawtube; and
    a controller, coupled to the pressure sensor, that adjusts the flow rate of the sample fluid from the sample container into the interrogation zone by controlling at least one of the flow rates of the sheath fluid and the waste fluid.

2. The fluidic system of claim 1, wherein the controller adjusts the flow rate of the sample fluid based on the measured pressure differential.

3. The fluidic system of claim 1, further comprising a motor with motor controls coupled to at least one of the sheath and waste pumps, wherein the controller is coupled to the motor controls.

4. The fluidic system of claim 3, further comprising a second motor with second motor controls, wherein the first motor with first motor controls is coupled to the sheath pump and the second motor with second motor controls is coupled to the waste pump, and wherein the controller is coupled to the first and second motor controls.

5. The fluidic system of claim 3, wherein the controller adjusts the flow rate of the sample fluid by adjusting the flow rate of the sheath fluid from the sheath container into the interrogation zone.

6. The fluidic system of claim 5, wherein the controller adjusts the flow rate of the sample fluid by adjusting the flow rate of the sheath fluid from the sheath container to the interrogation zone while simultaneously maintaining a substantially consistent flow rate of the waste fluid from the interrogation zone into the waste container.

7. The fluidic system of claim 6, wherein the controller is a proportional-integral-derivative (PID) controller.

8. The fluidic system of claim 1, wherein the first fluidic capacitor is selected from the group consisting of bellows-type and flexible tube-type.

9. The fluidic system of claim 1, wherein the second fluidic capacitor is selected from the group consisting of bellows-type and flexible tube-type.

10. The fluidic system of claim 1, further comprising a first check-valve located between the first fluidic capacitor and the interrogation zone and a second check-valve located between the interrogation zone and the second fluidic capacitor.

11. The fluidic system of claim 1, wherein the sheath pump is a peristaltic pump.

12. The fluidic system of claim 11, wherein the waste pump is a peristaltic pump.

13. The fluidic system of claim 1, wherein the waste pump is located relative to the interrogation zone such that the waste pump is configured to pump a combination of sample fluid and sheath fluid.

14. The fluidic system of claim 1, wherein the sheath pump and waste pump cooperate to create a fluidic pressure differential.

15. The fluidic system of claim 1, further comprising a flow meter that measures the flow rate of the sample fluid from the sample container into the interrogation zone, wherein the controller is coupled to the flow meter and adjusts the flow rate of the sample fluid based on the measured flow rate.

16. A method for pumping sheath fluid from a sheath container and sample fluid from a sample container into an interrogation zone of a flow cytometer, comprising the steps of:
    simultaneously pumping sheath fluid from the sheath container into the interrogation zone of the flow cytometer and pumping waste fluid from the interrogation zone into the waste container, wherein the flow rate of the sheath fluid is different from the flow rate of the waste fluid thereby drawing sample fluid through a drawtube coupled to the sample container;
    measuring, with a pressure sensor, a pressure differential of the sample fluid between the top of the drawtube and the bottom of the drawtube; and
    attenuating pulsations within the sheath fluid between the sheath pump and the interrogation zone;
    attenuating pulsations within the waste fluid between the interrogation zone and the waste pump;
    adjusting the flow rate of the sample fluid from the sample container into the interrogation zone based on the measured pressure differential, wherein adjusting the flow rate of the sample fluid includes adjusting at least one of the flow rate of the sheath fluid from the sheath container into the interrogation zone and the flow rate of the waste fluid from the interrogation zone into the waste container.

17. The method of claim 16, wherein adjusting the flow rate of the sample fluid from the sample container includes adjusting the flow rate of the sheath fluid from the sheath container into the interrogation zone.

18. The method of claim 17, wherein adjusting the flow rate of the sample fluid from the sample container includes adjusting the flow rate of the sheath fluid from the sheath container to the interrogation zone while simultaneously maintaining a substantially consistent flow rate of the waste fluid from the interrogation zone into the waste container.

* * * * *